(12) United States Patent
Pacifico

(10) Patent No.: US 9,931,468 B1
(45) Date of Patent: Apr. 3, 2018

(54) COMBINED MIXING AND DISPENSING DEVICE FOR SURGICAL MATERIAL

(71) Applicant: Abyrx Inc., Irvington, NY (US)

(72) Inventor: John Pacifico, Irvington, NY (US)

(73) Assignee: Abyrx Inc., Irvington, NY (US)

( * ) Notice: Subject to any disclaimer, the term of this patent is extended or adjusted under 35 U.S.C. 154(b) by 18 days.

(21) Appl. No.: 15/340,052

(22) Filed: Nov. 1, 2016

Related U.S. Application Data

(60) Provisional application No. 62/249,629, filed on Nov. 2, 2015.

(51) Int. Cl.
| | | |
|---|---|---|
| *A61B 17/88* | (2006.01) | |
| *A61M 5/20* | (2006.01) | |
| *B01F 7/00* | (2006.01) | |
| *B01F 13/00* | (2006.01) | |
| *B01F 15/00* | (2006.01) | |
| *B01F 15/02* | (2006.01) | |

(52) U.S. Cl.
CPC ............ *A61M 5/20* (2013.01); *B01F 7/0025* (2013.01); *B01F 13/002* (2013.01); *B01F 15/00162* (2013.01); *B01F 15/00188* (2013.01); *B01F 15/00207* (2013.01); *B01F 15/00246* (2013.01); *B01F 15/0289* (2013.01); *A61B 2017/8838* (2013.01); *A61M 2205/18* (2013.01); *A61M 2205/32* (2013.01); *A61M 2205/3306* (2013.01); *A61M 2205/3331* (2013.01); *A61M 2205/3368* (2013.01); *A61M 2205/3379* (2013.01); *A61M 2205/50* (2013.01); *A61M 2205/502* (2013.01); *A61M 2205/52* (2013.01); *A61M 2205/581* (2013.01); *A61M 2205/582* (2013.01); *A61M 2205/583* (2013.01); *A61M 2205/8206* (2013.01); *B01F 2215/0029* (2013.01); *B01F 2215/0034* (2013.01)

(58) Field of Classification Search
CPC .... A61B 2017/8844; A61B 2017/8838; A61B 17/8802; B01F 7/0025; B01F 15/00246
See application file for complete search history.

(56) References Cited

U.S. PATENT DOCUMENTS

| | | | |
|---|---|---|---|
| 5,876,116 A | 3/1999 | Barker et al. | |
| 5,961,211 A | 10/1999 | Barker et al. | |
| 6,033,105 A * | 3/2000 | Barker ............... | A61B 17/8816 222/241 |
| 6,042,262 A | 3/2000 | Hajianpour | |
| 6,547,432 B2 | 4/2003 | Coffeen et al. | |
| 6,974,247 B2 | 12/2005 | Frei et al. | |
| 7,168,847 B2 | 1/2007 | Frei et al. | |
| 7,638,958 B2 | 12/2009 | Philipp et al. | |
| 7,658,537 B2 | 2/2010 | Coffeen et al. | |

(Continued)

FOREIGN PATENT DOCUMENTS

| | | |
|---|---|---|
| WO | WO-2013/036525 A2 | 3/2013 |
| WO | WO-2013/036525 A3 | 3/2013 |

*Primary Examiner* — David Bates
(74) *Attorney, Agent, or Firm* — Mintz Levin Cohn Ferris Glovsky and Popeo, P.C.; Muriel Liberto, Esq.

(57) ABSTRACT

A device is described that can accept two or more components for mixing and preparing a composition within the device. Once mixed and prepared, the device can deliver the composition to a surgical site. The composition can be a putty-like material that sets over time at the surgical site, such as a hemostatic device or a device for sealing a hole or cavity in bone.

17 Claims, 1 Drawing Sheet

(56) References Cited

U.S. PATENT DOCUMENTS

| | | |
|---|---|---|
| 8,657,482 B2 | 2/2014 | Malackowski et al. |
| 8,992,071 B2 | 3/2015 | Vogt |
| 2007/0085496 A1* | 4/2007 | Philipp ................ A61B 17/151 |
| | | 318/139 |
| 2007/0211565 A1* | 9/2007 | Plishka .............. A61B 17/8822 |
| | | 366/189 |

* cited by examiner

COMBINED MIXING AND DISPENSING DEVICE FOR SURGICAL MATERIAL

TECHNICAL FIELD

The subject matter described herein relates to a device that can prepare and dispense a viscous surgical material to a surgical site.

BACKGROUND

Multi-component surgical materials, such as bone cements and similar compositions, must be thoroughly blended together to achieve the required composition and/or consistency for application to the surgical site and to ensure that the component parts of the material are completely mixed. Once thoroughly blended, the material must be dispensed to the surgical site. It is advantageous to perform both the mixing and delivery functions in a single device in order to improve efficiency and reduce the risk of contamination or loss of the surgical material.

While many multi-component surgical materials consist of two liquids or a liquid and a solid, certain materials consist of two or more solid materials which must be thoroughly blended before use, for example, the materials described in WO 2013/036525. Where the component materials are of a highly viscous putty-like consistency, it has been necessary to mix them by hand, for example, by kneading, prior to use. But hand-mixing can be time consuming and result in surgical materials that are inadequately or incompletely mixed. The result may be a composition having a consistency that is less than optimal for application to the wound site. Incomplete mixing may also result in a composition that will not fully and uniformly cure into the desired hardened material following its application to the wound site. In addition, it may be necessary to transfer the composition to another device for application to the surgical site, which can be cumbersome, time consuming, and risks loss and/or contamination of the composition.

The present invention addresses the need for improved means to ensure the thorough blending and efficient extrusion to a desired surgical location of a multi-component surgical material having highly viscous solid components.

DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

SUMMARY OF THE INVENTION

Figure 1A:
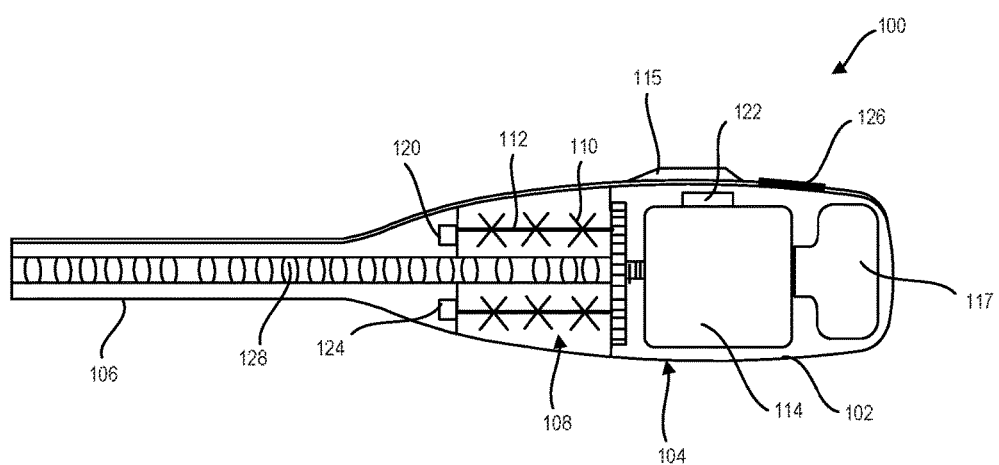
FIG. 1A shows a diagram illustrating features of an implementation of a mixing and delivery device consistent with implementations of the current subject matter.

In embodiments, the present disclosure provides a device comprising a body including a handle with an elongated nozzle extending from the handle; a mixing chamber disposed within the body for accepting and mixing at least two components of a composition for delivery to a surgical site; mixing blades disposed in the mixing chamber for mixing the at least two components, a motor coupled to the mixing blades via a mixing shaft, the motor having a first setting for rotating the mixing blades in a first direction and a second setting for rotating the mixing blades in a second direction; an extruder extending between the mixing chamber and a distal end of the elongated nozzle, the extruder assisting with extruding the composition from the mixing chamber and out of the distal end of the elongated nozzle. a sensor for collecting sensed data representing a characteristic of the at least two components or composition; and a processor in communication with the sensor for analyzing the sensed data and, based on the analyzed sensed data, controlling at least one of a rotational speed and rotational direction of the motor.

In embodiments, the mixing blades mix the composition when rotating in the first direction, and extrude the composition from the mixing chamber when rotating in the second direction.

In embodiments, the mixing chamber includes a hatch having an open position for accepting the one or more components into the mixing chamber, and a closed position for providing a sealed and sterile environment within the mixing chamber.

In embodiments, a part of the elongated nozzle is radiopaque.

In embodiments, the sensor collects viscosity data of the composition.

In embodiments, the sensor is a temperature sensor.

In embodiments, the sensor is a pressure sensor.

In embodiments, the sensor is an optical sensor.

In embodiments, the sensor detects a volume of the composition within the device.

In embodiments, the device further comprises a user interface on the body to display information related to the mixing or the extruding of the composition.

In embodiments, the device further comprises a switch on the handle for changing the rotational speed or the rotational direction.

In embodiments, the device further comprises a transport screw that extends along at least a part of a length of the elongated nozzle. In embodiments, the transport screw is rotatable.

In embodiments, the device further comprises an extending tip releasably coupled to the distal end of the elongated nozzle.

In embodiments, the device further comprises an alarm in communication with the processor.

In embodiments, the device further comprises a feedback mechanism in communication with the processor to alert a user that mixing of the composition is completed based on the sensed data, the feedback mechanism being audible, visual, or tactile.

In embodiments, the device is sterile or sterilizable.

DETAILED DESCRIPTION

The current subject matter is directed to various implementations of a mixing and delivery device that can accept two or more highly viscous components, e.g., putties, for mixing into a uniform composition and for extruding the composition from the device to a surgical site. The term "putty" refers to a soft, moldable, preferably non-elastic, cohesive composition. For example, the components can be mixed to form a settable composition that can be delivered, via a distal end of the device, to a surgical site within a patient.

The mixing and delivery device described herein is a single hand-held unit that both mixes a multi-component surgical material of highly viscous putty-like components and delivers the fully blended composition to the surgical site, thus eliminating the need for a surgeon to hand-mix the components and then transfer the resulting composition to a delivery device.

In some implementations, the mixing and delivery device can include one or more sensors, such as for sensing characteristics of the composition such as its viscosity. The mixing and delivery device can also include a timer element to monitor the time of mixing. The mixing and delivery device can also include a processor that can control the time and speed of the mixing to ensure that the components are optimally blended before extrusion. The processor may also control the settings of the device, such as in response to analyzed sensed data from a sensor and/or as a result of pre-programmed settings. The mixing and delivery device can also include a user-interface that can, for example, provide a user with information, such as information related to either the mixing or delivery of the composition. The mixing and delivery device can also include a single switch can turn the device on or off and optionally be toggled between mixing and extrusion modes.

In embodiments, time of mixing is between 30 to 90 seconds at an rpm of 1-4. In embodiments, the time of mixing is 45 s, 50 s, 60 s, 70 s, 80 s, or 90 s at an rpm of 1-4. In embodiments, the time of mixing is between 30-50 s, 40-60 s, or 50-90 s at an rpm of 1-4.

FIG. 1A illustrates an implementation of the mixing and delivery device 100 including a body 102 having a handle 104 with an elongated nozzle 106 extending from the handle 104. The body 102 can include a mixing chamber 108 that can accept one or more components for mixing within the mixing chamber 108, thereby forming a composition that can be extruded through and out a distal end of the nozzle 106.

The mixing chamber 108 can include at least one mixing blade 110 that can assist with mixing the components, thereby forming the composition within the mixing chamber 108. The mixing blade 110 can extend from and rotate along a mixing shaft 112 coupled to a motor 114. For example, the motor 114 can be located in the body 102, such as within the handle 104, and upon activation of the motor 114, the mixing shaft 112 can be forced to rotate. In some implementations, the motor 114 can rotate the mixing shaft 112 in more than one direction and at variable speeds. For example, the motor 114 can have a first setting that rotates the mixing shaft 112 and mixing blades 110 in a first direction (e.g., counter-clockwise) and a second setting that rotates the mixing shaft 112 and mixing blades 110 in a second direction (e.g., clockwise). The motor 114 can include other settings that correlate to various rotational speeds of the mixing shaft 112 and mixing blades 110. A switch 115 can be positioned along the handle 104 for easy manipulation of the motor, such as turning the motor on/off or changing the rotational direction or speed of the motor. In addition, the device 100 can include a battery 117 that can power the motor and also allow for easy maneuverability of the device 100. Alternatively or in addition, the device 100 can include a power cord for allowing an external source power the device 100.

In embodiments, the blades are static blades attached to the wall of the mixing chamber 108 or the blades consist of two sets of counter-rotating blades.

In embodiments, the device, or portions thereof, are sterile or sterilizable. In embodiments, the portions of the device that come into contact with the surgical material are sterile or sterilizable. In embodiments, the device is disposable. In embodiments the device, or a portion thereof, is reuseable. For example, the portion of the device containing the motor is reusable.

Figure 1B:
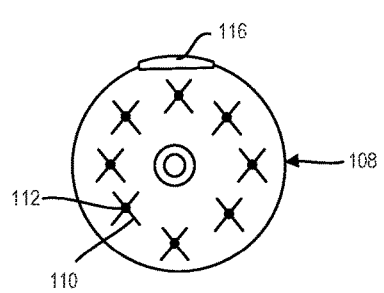
FIG. 1B shows a cross section of the mixing chamber, including mixing blades and a hatch for accessing the inside of the mixing chamber.

FIG. 1B illustrates a cross-section view of a mixing chamber 108, which show mixing blades 110 positioned within the mixing chamber 108 for mixing components of the composition. In addition, FIG. 1B shows a hatch 116 that can provide access to the mixing chamber 108. For example, in an open position, the hatch 116 can allow a user to introduce one or more components into the mixing chamber 108. In the closed position, the hatch 116 can assist with providing a sealed and sterile environment within the mixing chamber 108.

Any number of mixing blades 110 and mixing shafts 112 can be included in the mixing and delivery device 100 for assisting with mixing the components within the mixing chamber 108. The mixing blades 110 can have any number of shapes and sizes, such as shapes that are conducive for mixing viscous material. In addition, any number of a variety of motors 114 can be included in the device, such as a motor 114 that can provide variable torque and/or variable rotational speed. Either the torque or the rotational speed can be controlled by a user of the device or a processor associated with the device. For example, the motor can rotate the shaft at approximately 15 rpm to approximately 250 rpm in either direction. The components that can be mixed in the mixing chamber can include a liquid, gel, powder, paste, particle, putty and any combinations thereof.

The mixing and delivery device 100 can include a variety of features for assisting with preparing and dispensing the composition. For example, the device 100 can include one or more sensors 120 that can detect a variety of characteristics related to either the composition or the device 100. For example, some implementations of the device 100 can include a temperature sensor for detecting the viscosity of the material within the mixing chamber 108. Other sensors 120, such as pressure and optical sensors can be included in the mixing and delivery device 100, which can detect a volume of composition within and/or dispensed from the device 100.

In some implementations, the device 100 can include a processor 122 that is in communication with the motor 114 and/or sensors 120. As such, the processor 122 can analyze the sensed data collected from the sensors 120 in order to determine one or more appropriate settings. For example, the processor 122 can compare sensed data collected from a sensor 120 located adjacent the mixing chamber 108. The processor 122 can continually analyze sensed data and can automatically, based on the analyzed sensed data, adjust one or more variable settings associated with the device 100.

In some implementations, the processor can determine (based on analyzed sensed data or based on a pre-programmed time of mixing) that the composition is ready for dispensing, such as that the components have been sufficiently mixed and the composition is of an optimal consistency for extrusion and application to the surgical site. As such, the processor 122 can signal to the user, for example using a visual or audio signal, that the composition is fully blended and ready for use. The user may then toggle a switch on the device from mixing to extrusion mode in order to extrude the composition from the device to the surgical site. In extrusion mode, the mixing shaft 112 rotates in a direction that causes the composition to be dispensed from the mixing chamber 108. For example, rotation of the mixing blades 110 in a first direction can cause the composition to be mixed, and rotation of the mixing blades 110 in a second (opposite) direction can cause the composition to be dispensed from the mixing chamber 108, as discussed above. Therefore, based on the processor's analysis of sensed data or the elapsed time of mixing, the processor 122 can control the mixing and/or the composition and alert the user when the composition is ready for use.

The composition can be advanced from the mixing chamber 108 and along the elongated nozzle 106 in order to be dispensed from the device 100 at a distal end of the elongated nozzle 106. Any number of a variety of extruder related features and functions can be implemented into the device 100 for assisting with dispensing the composition from the mixing chamber 108 and out of the device 100.

For example, as shown in FIG. 1A, the elongated nozzle 106 can include a transport screw 128 that extends along at least a part of the length of the elongate nozzle 106. As such, the mixing blades 110 can be caused to rotate in a direction that forces the composition out of the mixing chamber 108 and along the transport screw 128 until being dispensed at the distal end of the elongated nozzle 106. In some implementations, the transport screw 128 can rotate, thereby further assisting with transporting the composition along and out the elongated nozzle 106. In some embodiments, the transport screw is configured such that it rotates only during transport and not during mixing. In some embodiments, the transport screw is configured to rotate in the counter-transport direction during mixing. In some embodiments, there is a port between 108 and 128.

In some implementations, the device 100 can include a piston, such as a hydraulically-driven piston, that can assist with advancing the composition along and out the elongated nozzle 106.

In some implementations, the device 100 can include an elongated nozzle attached to the distal end of 106 that is flexible and/or includes a beveled distal end. A part of the elongated nozzle can be radiopaque for allowing visualization under fluoroscopy.

Figure 1C:
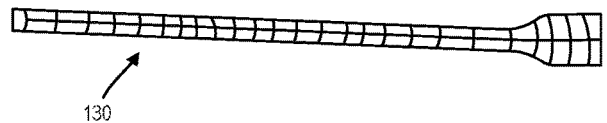
FIG. 1C shows a diagram illustrating an extending tip.

FIG. 1C illustrates an extending tip 130 that can be releasably coupled to the distal end of the elongated nozzle 106. The extending tip 130 can include a first coupling feature that mates with a second coupling feature associated with the elongated nozzle 106. The coupling features can allow for the extending tip 130 to releasably couple to the elongated nozzle 106. The extending tip 130 can have a reduced diameter compared to the elongated nozzle 106 and/or can provide additional length to the elongated nozzle 106. Extruding features for delivering the composition from the mixing chamber 108 can be included and/or extended into the extending tip 130 for assisting with dispensing the composition from a distal end of the extending tip 130.

In some implementations, the mixing and delivery device 100 can provide a variety of feedbacks, such as visual, audible and/or tactile feedback to allow the user to easily receive information related to either the preparation or delivery of the composition. In turn, this information can allow the user to easily control the contents and delivery mechanisms of the device 100. For example, the device 100 can provide an audible noise when the composition begins to dispense from the distal end of the elongated nozzle 106. This can allow the user to know when such dispensing begins, which would otherwise be difficult or impossible for the user to know because the distal end may be out of sight from the user (e.g., located in a patient at the surgical site).

An example method associated with the device 100 can include the device 100 informing the user once the mixing/kneading of the composition is completed. Such information can be provided, for example, on a user interface 126 or via a feedback mechanism (e.g., audible, visual, tactile, etc.). In addition, such information can be determined from the processor 122, such as by the processor analyzing sensed data collected by one or more sensors associated with the device 100. When the user and/or device 100 determines that the composition is ready for dispensing, the motor 114 can be activated to rotate the mixing shaft 112 in a direction that causes the mixing blades 110, transport screw 128, and/or piston to advance the composition from the mixing chamber 108 and out of the distal end of the elongated nozzle 106. The user and/or the processor 122 can control the rotational speed and direction of rotation of the motor 114 in order to control the rate and quantity of composition dispensed. In addition, if any programmed processes are violated, such as if the composition is left in the mixing chamber 108 for too long or mixes for too long, then an alarm can be provided (e.g., visual and/or audio) for alerting the user. Information related to the violated process can also be displayed on the user interface 126.

In addition to mixing the component parts of the composition, the device may also be used to mix active agents, such as active pharmaceutical ingredients or biologics, into the composition, or to add cells or tissue derived material to the composition.

One or more aspects or features of the subject matter described herein can be realized in digital electronic circuitry, integrated circuitry, specially designed application-specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical discs, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as, for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described above can be directed to various combinations and sub-combinations of the disclosed features and/or combinations and sub-combinations of one or more features further to those disclosed herein. In addition, the logic flows depicted in the accompanying figures and/or described herein do not necessarily require the particular order shown, or sequential order, to achieve desirable results. The scope of the following claims may include other implementations or embodiments.

What is claimed is:

1. A device comprising:
   a body including a handle with an elongated nozzle extending from the handle;
   a mixing chamber disposed within the body for accepting and mixing at least two components of a composition for delivery to a surgical site;
   mixing blades disposed in the mixing chamber for mixing the at least two components,
   a motor coupled to the mixing blades via a mixing shaft, the motor having a first setting for rotating the mixing blades in a first direction and a second setting for rotating the mixing blades in a second direction;
   an extruder extending between the mixing chamber and a distal end of the elongated nozzle, the extruder assisting with extruding the composition from the mixing chamber and out of the distal end of the elongated nozzle;
   a sensor for collecting sensed data representing a characteristic of the at least two components or composition; and
   a processor in communication with the sensor for analyzing the sensed data and, based on the analyzed sensed data, controlling at least one of a rotational speed and rotational direction of the motor.

2. The device of claim 1, wherein the mixing blades mix the composition when rotating in the first direction, and extrude the composition from the mixing chamber when rotating in the second direction.

3. The device of claim 1, wherein the mixing chamber includes a hatch having an open position for accepting the one or more components into the mixing chamber, and a closed position for providing a sealed and sterile environment within the mixing chamber.

4. The device of claim 1, wherein a part of the elongated nozzle is radiopaque.

5. The device of claim 1, wherein the sensor collects viscosity data of the composition.

6. The device of claim 1, wherein the sensor is a temperature sensor.

7. The device of claim 1, wherein the sensor is a pressure sensor.

8. The device of claim 1, wherein the sensor is an optical sensor.

9. The device of claim 1, wherein the sensor detects a volume of the composition within the device.

10. The device of claim 1, further comprising a user interface on the body to display information related to the mixing or the extruding of the composition.

11. The device of claim 1, further comprising a switch on the handle for changing the rotational speed or the rotational direction.

12. The device of claim 1, further comprising a transport screw that extends along at least a part of a length of the elongated nozzle.

13. The device of claim 12, wherein the transport screw is rotatable.

14. The device of claim 1, further comprising an extending tip releasably coupled to the distal end of the elongated nozzle.

15. The device of claim 1, further comprising an alarm in communication with the processor.

16. The device of claim 1, further comprising a feedback mechanism in communication with the processor to alert a user that mixing of the composition is completed based on the sensed data, the feedback mechanism being audible, visual, or tactile.

17. The device of claim 1, wherein the device is sterile or sterilizable.

* * * * *